United States Patent [19]

Wilheim et al.

[11] Patent Number: 5,093,518
[45] Date of Patent: Mar. 3, 1992

[54] GLYCEROL DERIVATIVES, THEIR PREPARATION PROCESS, CROSS-LINKING COMPOSITIONS CONTAINING THEM, AND THEIR USE IN THE TEXTILE INDUSTRY

[75] Inventors: Didier Wilheim, Issy les Moulineaux; Fernand Cuirassier, Saint-Denis; Alain Blanc, Paris, all of France

[73] Assignee: Societe Francaise Hoechst, Puteaux, France

[21] Appl. No.: 463,192

[22] Filed: Jan. 10, 1990

[30] Foreign Application Priority Data

Feb. 23, 1989 [FR] France ............................... 89 02341

[51] Int. Cl.$^5$ ................................................ C07C 69/66
[52] U.S. Cl. ................................................ 560/177
[58] Field of Search ........................................ 560/177

[56] References Cited

U.S. PATENT DOCUMENTS 4,010,183  3/1977  Quada ........................... 260/410.8
4,654,370  3/1987  Marnott, III et al. ............ 260/410.8
4,990,289  2/1991  Shoyab et al. ................... 260/410.8

Primary Examiner—Bruce Gray
Attorney, Agent, or Firm—Browdy and Neimark

[57] ABSTRACT

Glycerol derivatives of general formula (I)

$$CH_2-OR$$
$$CH-OR_1 \qquad (I)$$
$$CH_2-OR_2$$

in which R = allyl, methylallyl, acryloyl or methacryloyl, $R_1 = R_2 =$ glyoxyloyl, $R_1$, $R_2 =$ H, glyoxyloyl; their preparation process, their use as cross-linking agents and cross-linking or cross-linkable compositions containing them.

Application in the textile or paper industry.

8 Claims, No Drawings

GLYCEROL DERIVATIVES, THEIR PREPARATION PROCESS, CROSS-LINKING COMPOSITIONS CONTAINING THEM, AND THEIR USE IN THE TEXTILE INDUSTRY

The present invention relates to new derivatives of glycerol, their preparation process, their use as cross-linking agents, the cross-linking and cross-linkable compositions containing them and their use in the textile industry.

Copolymers capable of being made insoluble by cross-linking have been known for a long time. This cross-linking is generally obtained by introduction into a mixture of monomers to be copolymerised of a monomer containing one or more reactive groups such as the following groups: carboxyl, vinyl, hydroxyl, oxirane, optionally substituted carbamoyl, optionally etherified carboxyhydroxymethyl, such as for example N-methylolacrylamide, acrylamidoglycolic acid, methylenebisacrylamide, 1,2-diacryloylamino-1,2-dihydroxyethane, tetraallyloxyethane, glycidyl methacrylate.

Certain copolymers can be cross-linked simply by heating generally in the presence of an acid catalyst or a catalyst capable of liberating an acid, this is the case, for example, for the following copolymers; acrylic, vinylic or acrylvinylic containing as a cross-linking agent methylol amides, of unsaturated organic acids such as acrylic, methacrylic and maleic acids.

However, certain of these cross-linking monomers possess the property of liberating either during their polymerisation, or at the time of their cross-linking, traces of formaldehyde of which the inconveniences are known today: others are either insoluble in water or only slightly reactive, or difficult to incorporate in the desired copolymer. Now the present invention has in particular as its subject the provision of new cross-linking agents that obviate these inconveniences.

The new cross-linking agents according to the present invention are glycerol derivatives of general formula (I):

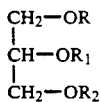

in which R represents an allyl, methylallyl, acryloyl or methacryloyl group and $R_1$ and $R_2$ are either identical, representing a glyoxyloyl group, or different, representing a hydrogen atom or a glyoxyloyl group.

The invention has more particularly as a subject the glycerol derivatives as those defined previously characterised in that in the said formula (I), R represents an allyl, acryloyl or methacryloyl group and $R_1$ and $R_2$ keep the meaning given previously.

Among these last products, the invention has in particular as a subject:
3-acryloyloxy-2-glyoxyloyloxy-1-propanol;
1-acryloyloxy-3-glyoxyloyloxy-2-propanol;
1-acryloyloxy-2,3-diglyoxyloyloxy-propane;
3-methacryloyloxy-2-glyoxyloyloxy-1-propanol;
1-methacryloyloxy-3-glyoxyloyloxy-2-propanol;
1-methacryloyloxy-2,3-diglyoxyloyloxy-propane;
3-allyloxy-2-glyoxyloyloxy-1-propanol;
1-allyloxy-3-glyoxyloyloxy-2-propanol.

According to the invention, the derivatives of general formula (I) above can be prepared by a process characterised in that glyoxylic acid is reacted with a substituted oxirane of general formula (II):

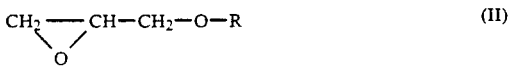

in which R has the meaning indicated previously, to obtain a product of general formula (I) as defined above:

In the preferred conditions of employing the invention process, the process described above is achieved in the following manner:

The reaction of glyoxylic acid with substituted oxirane of general formula (II) is effected:

at a temperature contained between 50° C. and 120° C., advantageously at around 80° C.;

with an excess of substituted oxirane of general formula (II);

with glyoxylic acid in aqueous solution, advantageously with an aqueous solution of glyoxylic acid of $75 \pm 10\%$ by weight;

in the presence of a catalyst either a chromium derivative catalyst such as chromium acetylacetonate, or preferably a basic catalyst such as a tertiary amine such as triethylamine or dimethyllaurylamine;

in the possible presence of a solvent such as an aliphatic or aromatic hydrocarbon, by eliminating, at the end of the reaction, the excess of substituted oxirane used by washing the reaction medium, diluted with water, with a compatible organic solvent, non miscible with water, preferably diethyl oxide.

The product of general formula (I) can be identified due to the preparation of a characteristic derivative of its aldehyde function or functions such as an oxime, O-methyl oxime, phenylhydrazone, dinitrophenylhydrazone, according to the standard methods of preparation of these derivatives.

For example, the sought product of general formula (I) can be identified by isolation of its O-methyl oxime or oximes obtained by reacting in an aqueous medium, an excess of methoxyamine hydrochloride on the crude reaction mixture, the non transformed starting oxiran of which that has been eliminated, beforehand. The O-methyl oxime or O-methyl oximes thus obtained can be purified by intrinsically known means such as distillation, chromatography, etc.

The present application has equally as a subject the use of derivatives of general formula (I) as defined above as cross-linking agents.

As cross-linking agents, the derivatives of formula (I) according to the invention can advantageously enter into a cross-linking composition and/or cross-linkable composition, containing at least one glycerol derivative as defined above copolymerisable with at least one monomer copolymerisable with this derivative.

It is thus that the presence in this derivative of the glycerol with an ethylene bond allows its polymerisation or its copolymerisation with other monomers whilst conserving its cross-linking activity. It is likely that the glyoxyloyl group(s) present in this glycerol derivative react on the hydroxyl groups of polymers or copolymers formed to constitute acetal bridges and cross-link in this way the macromolecules, for as will be shown further on, the composition according to the invention behaves differently to a simple mixture.

Advantageously, the monomers that can be copolymerised with a derivative of formula (I) according to the invention to give copolymers which themselves are able to enter into a cross-linking reaction, contain acrylic or methacrylic monomers such as $C_1-C_{10}$ alkyl acrylates and methacrylates, vinyl ethers and esters such as vinyl acetate, vinyl propionate, vinyl chloride, (meth)acrylic acid, and its alkali metal or ammonium salts, acrylonitrile, styrene or substituted olefins such as vinylsulphonic acid, preferably salified in the form of the sodium salt. Mixtures of these monomers can equally be used.

This copolymerisation of the glycerol derivative of general formula (I) with other unsaturated monomers can be carried out in dispersion, in emulsion, in solution either by a batch process, or by semi-continuous or continuous processes, according to known methods, in the presence of one or more polymerisation initiators such as a Redox system, an azo-compound, a peroxide and/or a hydroperoxide. The proportion of the cross-linking agent introduced into the copolymer can vary greatly from 0.1 to 15% by weight, preferably from 0.5 to 5% by weight relative to the total weight of monomers employed.

The cross-linking and/or cross-linkable copolymers are obtained by copolymerising the glycerol derivative used as cross-linking agent prepared previously. The choice of monomers entering into the copolymerisation allows the modification of certain physical properties of the substances obtained after cross-linking, such as the flexibility, the hardness, the colouration. The introduction into the copolymer of reactive groups such as hydroxyl, carboxyl, carbamoyl or other groups, can usefully reinforce the cross-linking properties. The cross-linking effect can equally be reinforced by the addition of known catalysts such as acids, ammonium salts or mineral or organic salts of metals having several valencies, such as for example, chlorides, nitrates of magnesium, zinc, calcium, aluminum, zirconium.

To show the cross-linking capability of cross-linking and/or cross-linkable compositions according to the invention, the property of these compositions to give, by simple heating, films resistant to organic solvents, is brought to the fore. The heating produces a cross-linking within the macromolecules of the copolymer or between the macromolecules of the copolymer.

The properties of cross-linking and/or cross-linkable compositions of the invention make them more particularly interesting in the textile industry or in the paper industry. These compositions are in effect usable for the realisation of fibre or non-woven mats or to improve the effects of crease-resistance treatments of fabrics. They allow in particular the obtaining of fabrics, woven or non-woven, that resist well organic solvents, in particular organic solvents used in dry-cleaning operations and increase the resistance to abrasion and creasing as well as the permanence during washing of treatments intended to give the fabric crease-resistance, thus they allow the obtaining of crease-resistant fabrics due to the treatment of a fabric containing cellulosed threads or fibres with the aid of such a composition.

The following examples are given as illustrations and in no way limit the invention. In these examples, the physical chemistry controls are achieved as follows:

the dry extract, expressed in percentage by weight, is determined by drying 1 g of dispersion for 3 hours at 105° C.;

the Brookfield viscosity is determined at 20°-22° C. with an RVT Brookfield viscometer equipped with the 1 axis at a speed of 50 revs/min.;

the swelling ratio, SR, is determined at ambient temperature by immersion in trichloroethylene of a flat circular test piece of 50 mm diameter cut from a dry film, of approximately 0.5 mm in thickness, of the dispersion to be tested. The SR is measured simultaneously on a non-thermically treated film and on a film treated for 10 minutes at 150° C. The SR is calculated by the relationship $$SR = \frac{100\,(fd - id)}{fd}$$

in which id is the initial diameter of the test piece and fd is the final diameter;

the NMR spectra are determined on a Brucker AC 200 apparatus (50 MHz $^{13}C$ and 200 MHz $^1H$). The chemical displacements are expressed in ppm relative to tetramethylsilane.

EXAMPLE 1

Preparation of 1-methacryloyloxy-3-glyoxyolyoxy-2-propanol, and 3-methacryloyloxy-2-glyoxyloyloxy-1-propanol.

The following are heated with agitation for 3 hours at 80° C.:

300 g (2.11 moles) of glycidyl methacrylate;
48.8 g (0.53 moles) of monohydrated glyoxylic acid;
5.36 (53 mmoles) of triethylamine;
0.15 g of paramethoxyphenol;

then the reaction medium is cooled down to ambient temperature. In this way an oily solution designated Ac is obtained and is used as it is. In order to characterise the products present in the solution Ac, it is poured into a mixture of 355 g of water and 355 g of diethyl oxide. After decanting, the aqueous phase is washed twice with 355 g of diethyl oxide and the ether phase is washed twice with 355 g of water. From the reunited ether phases, after the elimination of the diethyl oxide, 156 g (1.1 mole) of non-transformed glycidyl methacrylate is isolated. The reunited aqueous phases are concentrated under vacuum to a total weight of 1140 g, designated hereafter solution A. 19 g (0.23 mole) of methoxyamine hydrochloride is introduced into 100 g of this solution A then the solution obtained is left for 2 hours at ambient temperature.

In this way a milky suspension is obtained which is washed twice with 136 g of dichloromethane, then the chloromethylenic phases are reunited, dried over anhydrous magnesium sulphate and finally concentrated under vacuum. In this way 7.5 g of a yellow oil is isolated which is purified by preparative chromatography on a column (500×25) filled with silica of a size grading of 10 micrometers, eluting with a hexane-ethyl acetate mixture 8/2 by volume, which allows the isolation on the one hand of, 5 g (20.4 mmoles) of 1-methacryloyloxy-3-methoxyiminoacetoxy-2-propanol, and on the other hand of, 2 g (8.15 mmoles) of 3-methacryloyloxy-2-methoxyiminoacetoxy-1-propanol characterised by their $NMR^1H$ spectra registered in deuterized chloroform.

1-methacryloyloxy-3-methoxyiminoacetoxy-2-propanol (diastereoisomer mixture 50/50).

7.49 ppm, s, 1H, CH=N—
6.13 ppm, m, 1H, $CH_2$=C
5.60 ppm, m, 1H, $CH_2$=C 4.39–4.16 ppm, m, 5H —CH$_2$—CH—CH$_2$—
4.04 ppm, s, 3H, OCH$_3$
2.7 ppm, s, 1H, OH
1.93 ppm. m. 3H, CH$_3$—C=
3-methacryloyloxy-2-methoxyiminoacetoxy-1-propanol (mixtures of isomers)

|  | isomers | |
| --- | --- | --- |
|  | majority | minority |
| —CH=N, s, 1H | 7.46 ppm | 7.49 ppm |
| CH$_2$=C, m, 1H | 6.11 ppm | 6.09 ppm |
| CH$_2$=C, m, 1H | 5.58 ppm | 5.58 ppm |
| —CH—O—CO—, quintuplet, 1H, J=4.9Hz | 5.23 ppm | 5.30 ppm |
| —CH$_2$—O—CO—, m, 2H | 4.48 ppm | 4.42–4.3 ppm |
| —OCH$_3$, s, 3H | 4.02 ppm | 4.02 ppm |
| —CH$_2$OH, d, 2H, J=4.9Hz | 3.78 ppm | 3.80 ppm |
| —OH, s, 1H | 2.60 ppm | 2.50 ppm |
| CH$_3$—C=, m, 3H | 1.91 ppm | 1.91 ppm |

Consequently, the solution A contains at least 50.28 g (0.23 mole) of 1-methacryloyloxy-3-glyoxyloyloxy-2-propanol and 20.1 g (93 mmoles) of 3-methacryloyloxy-2-glyoxyloyloxy-1-propanol that is a yield of 61% of the theoretical calculation relative to the glyoxylic acid employed.

EXAMPLE 2

Operating as in example 1, starting with 270.2 g (2.11 moles) of glycidyl acrylate, 48.8 g (0.53 mole) of monohydrated glyoxylic acid, 5.36 g (53 mmoles) of triethylamine and 0.15 g of paramethoxyphenol, a mixture of 1-acryloyloxy-3-glyoxyloyloxy-2-propanol and 3-acryloyloxy-2-glyoxyloyloxy-1-propanol is obtained with a yield greater than 65% of the theoretical calculation relative to the glyoxylic acid employed.

These products have been characterised by isolation of their O-methyl oxime using the process described in example 1.

1-acryloyloxy-3-methoxyiminoacetoxy-2-propanol

| Microanalysis | | C % | H % | N % |
| --- | --- | --- | --- | --- |
| C$_9$H$_{13}$NO$_6$ | calculated | 46.75 | 5.7 | 6.05 |
| Mol. Wt. = 231.2 | found | 46.5 | 5.8 | 6.2 |

Physical analysis: NMR$^1$H (CDCl$_3$). 7.51 ppm, s, 1H, CH=N. 6.44 ppm, dd, 1H, J=1.8 Hz and J=17 Hz, CH$_2$=C. 6.13 ppm, dd, 1H, J=17 Hz and J=10.3 Hz, CH—CO. 5.87 ppm, dd, 1H, J=1.8 Hz and J=10.3 Hz, CH$_2$=C. 4.29–4.20 ppm, m, 5H,

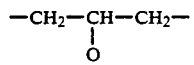

4.05 ppm, s, 3H, —OCH$_3$. 2.7 ppm, s, 1H, —OH.
3-acryloyloxy-2-methoxyiminoacetoxy-1-propanol
Physical analysis —NMR$^1$H (CDCl$_3$)

|  | isomers | |
| --- | --- | --- |
|  | majority | minority |
| —CH=N, s, 1H | 7.49 | 7.51 |
| CH$_2$=C, dd, 1H, J=1.8Hz and J=17Hz | 6.44 | 6.43 |
| =CH—CO, dd, 1H, J=17Hz and J=10.3Hz | 5.87 | 5.865 |
| CH—OCO, quintuplet, 1H, J=4.9Hz | 5.23 | 5.30 |
| COOCH$_2$, m, 2H | 4.53–4.43 | 4.46–4.40 |
| OCH$_3$, s, 3H | 4.06 | 4.06 |

|  | isomers | |
| --- | --- | --- |
|  | majority | minority |
| OH, d, 2H, J=4.9Hz | 3.83 | 3.83 |

EXAMPLE 3

Operating as in example 1, starting with 300 g (2.63 moles) of allyl and glycidyl oxide, 60.5 g (0.6575 mole) of monohydrated glyoxylic acid, 6.6 g (66 mmoles) of triethylamine and 150 mg of paramethoxyphenol, a mixture of 1-allyloxy-3-glyoxyloyloxy-2-propanol and 3-allyloxy-2-glyoxyloyloxy-1-propanol is obtained with a yield greater than 70% of the theoretical calculation relative to the glyoxylic acid employed.

These products have been identified by isolation of their O-methyl oxime according to the process described in example 1. The physical characteristics of these oximes are given hereafter.

1-allyloxy-3-methoxyiminoacetoxy-2-propanol
Physical analysis NMR$^1$H (CDCl$_3$). 7.47 ppm, s, 1H, CH=N. 5.90 ppm, m, 1H, =CH—C. 5.22 ppm, m, 2H, CH$_2$= 4.29 ppm. part AB of a system ABX, 2H, J$_{AB}$=11.5 Hz, J$_{AX}$=4.9 Hz, J$_{BX}$=6 HZ, O—CH$_2$. 4.05 ppm, m, 1H, CH—O. 4.02 ppm, s, 3H, OCH$_3$. 3.98 ppm, m, 2H, allyl CH$_2$. 3.48 ppm, part AB of a system ABX, 2H, J$_{AB}$=9.8 Hz. J$_{AX}$=4.5 Hz, J$_{BX}$=5.8 Hz, O—CH$_2$. 2.8 ppm, s, 1H, OH.

3-allyloxy-2-methoxyiminoacetoxy-1-propanol
Physical analysis NMR$^1$H (CDCl$_3$). 7.46 ppm, s, 1H, —CH=N. 5.78 ppm, m, 1H, =CH—. 5.17 ppm, m, 3H, CH$_2$= and CHOCO. 4.0 ppm, s, 3H, OCH$_3$. 3.95 ppm, m, 2H, =C—CH$_2$—O. 3.79 ppm, d, 2H, —CH$_2$—OH. 3.62 ppm, d, 2H, O—CH$_2$—CH—. 2.95 ppm s, 1H, OH.

EXAMPLE 4

A solution, designated S$_{14}$, is prepared by dissolving, with agitation, at ambient temperature, the following in 199.6 g of distilled water:

16.1 g of an aqueous solution at 28% by weight of the sodium salt ethoxylated laurylethersulphate with 3 to 4 moles of ethylene oxide.

33.8 g of an aqueous solution at 20% by weight oleocetyl alcohol with 25 moles of ethylene oxide;

1 g of sodium hydrogen carbonate;

1.2 g of potassium peroxodisulphate;

2.61 g of methacrylamide.

Simultaneously, a solution, designated S$_{24}$, is prepared by mixing the following, with agitation, at ambient temperature:

192.7 g of n-butyl acrylate;

245.85 g of methyl methacrylate;

2.25 g of acrylic acid;

21.10 g of solution Ac prepared in example 1.

In a polymerisation reactor, 250 g of distilled water is heated to 83° C., then with agitation, at this temperature, the solution obtained by mixing extemporaneously the two preceding solutions is introduced over 4 hours, then when the introduction is finished, the reaction medium is maintained with agitation at 83°±1° C. for one hour and then it is cooled down to ambient temperature.

After filtration through a sieve with a mesh size of 0.16 mm, an aqueous fluid dispersion, with a milky appearance is obtained, having a pH of 3.95, a dry extract of 47.76%, a Brookfield viscosity of 50 mPa.s, a particle size (average of the order z) of 172 nm, a swelling ratio, SR, of 122% and a swelling ratio after thermal treatment of 110%.

EXAMPLE 5

A solution, designated $S_{15}$, is prepared by dissolving the following in 273.6 g of distilled water, with agitation, at ambient temperature:

3.6 g of an aqueous solution at 50% by weight of a sodium salt of ether sulphate of ethoxylated tributylphenol with 7 moles of ethylene oxide;

4.5 g of an aqueous solution at 20% by weight of ethoxylated nonylphenol with 30 moles of ethylene oxide;

0.9 g of ethoxylated nonyphenol with 6 moles of ethylene oxide;

1 g of sodium hydrogen carbonate;

2.61 g of methacrylamide;

1.35 g of potassium peroxodisulphate.

Simultaneously, a solution designated $S_{25}$, is prepared, by mixing with agitation, at ambient temperature:

232.9 g of styrene;

205.7 g of n-butyl acrylate;

2.25 g of acrylic acid;

21.10 g of a solution Ac prepared in example 1.

In a polymerisation reactor, the following are heated to 82° C., with agitation:

250 g of distilled water;

0.45 g of an aqueous solution at 50% by weight of a sodium salt of ethersulphate ethoxylated tributylphenol with 7 moles of ethylene oxide, then the solution obtained by mixing extemporaneously solutions $S_{15}$ and $S_{25}$ is introduced over 4 hours, with agitation, maintaining the temperature at 84°±1° C. After the introduction is finished, the reaction medium is maintained for one hour at 80° C. with agitation then it is cooled down to ambient temperature and finally, it is filtered through a sieve with a mesh size of 0.16 mm. In this way a fluid dispersion is obtained with a milky appearance, having a pH of 3.35, a dry extract of 44.5%, a Brookfield viscosity of 38 mPa.s, a particle size (average of the order z) of 230 nm, a swelling ratio of 114% and a swelling ratio after thermal treatment of 110%.

EXAMPLE 6

A solution, designated $S_{16}$ is prepared by dissolving the following with agitation, at ambient temperature, in 209.7 g of distilled water:

27 g of an aqueous solution at 25% by weight of linear $C_{14}$-$C_{18}$ sodium alkanesulphonate;

11.25 g of an aqueous solution at 20% by weight of ethoxylated nonylphenol with 30 moles of ethylene oxide;

11.25 g of an aqueous solution at 20% by weight of ethoxylated oleocetylic alcohol with 25 moles of ethylene oxide;

0.68 g of sodium acetate;

0.90 g of potassium peroxodisulphate;

4.5 g of an aqueous solution at 29.7% by weight of sodium vinylsulphonate;

2.61 g of methacrylamide.

Simultaneously, a solution, designated $S_{26}$, is prepared by mixing the following with agitation, at ambient temperature:

137.9 g of vinyl acetate;

301.5 g of n-butyl acrylate;

21.1 g of solution Ac prepared in example 1.

250 g of distilled water is heated in a polymerisation reactor to 80° C., then at this temperature, with agitation, the following are introduced successively, in one operation: an aqueous solution containing 0.45 g of potassium peroxodisulphate in 10 g of water, then one minute later, an aqueous solution containing 0.5 g of sodium metabisuphite in 10 g of water and finally the solution obtained by mixing extemporaneously the previous solutions $S_{16}$ and $S_{26}$ is introduced over 4 hours with agitation, maintaining the temperature at 84° C. At the end of the introduction, the reaction medium is maintained for one hour with agitation at 84° C. then it is cooled down to ambient temperature and finally it is filtered through a sieve with a mesh size of 0.16 mm. In this way a fluid dispersion is obtained with a milky appearance, having a pH of 3.2, a Brookfield viscosity of 34 mPa.s, a particle size (average of the order of z) of 264 nm, a swelling ratio of 130% and a swelling ratio after thermal treatment of 110%.

EXAMPLE 7 FOR COMPARISON

A solution designated $S_{17}$ is prepared by dissolving the following with agitation at ambient temperature in 209.7 g of distilled water.

27 g of an aqueous solution at 25% by weight of linear $C_{14}$-$C_{18}$ sodium alkanesulphonate;

11.25 g of a aqueous solution at 20% by weight of ethoxylated nonylphenol with 30 moles of ethylene oxide;

11.25 g of an aqueous solution at 20% by weight of ethoxylated oleocetylic alcohol with 25 moles of ethylene oxide;

0.68 g of sodium acetate;

0.90 g of potassium peroxosulphate;

4.5 g of an aqueous solution at 29.7% by weight of sodium vinylsulphonate;

2.61 g of methacrylamide.

Simultaneously, a solution designated $S_{27}$ is prepared, by mixing the following with agitation, at ambient temperature:

137.9 g vinyl acetate;

301.5 g of n-butyl acrylate;

4.4 g (31 mmoles) of glycidyl methacrylate.

In a polymerisation reactor, 250 g of distilled water is heated to 80° C., then at this temperature, with agitation, the following are introduced successively, in one operation, an aqueous solution containing 0.45 g of potassium peroxodisulphate in 10 g of water, then one minute later, an aqueous solution containing 0.5 g of sodium metabisulphite in 10 g of water and finally the aqueous solution obtained by mixing extemporaneously the aforementioned solutions $S_{17}$ and $S_{27}$ is introduced over 4 hours, with agitation, maintaining the temperature at 84° C. At the end of the introduction, the reaction medium is maintained, with agitation, at 84° C. for one hour. Then the following is introduced with agitation:

—2.295 g (31 mmoles) of monohydrated glyoxylic acid, then the reaction medium is maintained, with agitation, at 83°±1° C. for one hour before being cooled down to ambient temperature and finally it is cooled down to ambient temperature and filtered through a sieve with a mesh size of 0.16 mm. In this way a fluid dispersion is obtained with a milky appearance, giving a film soluble in trichloroethylene, which shows the absence of cross-linking. Neither does this film show thermo-cross-linking when heated to 150° C.

EXAMPLE 8 FOR COMPARISON

Example 7 for comparison is reproduced except that the glycidyl methacrylate is replaced by an equivalent quantity of 2,3-dihydroxypropyl methacrylate, that being 4.96 g (31 mmoles).

At the end of the reaction, a fluid dispersion is obtained with a milky appearance, giving a film soluble in trichlorethylene, which shows the absence of cross-linking. Neither does this film show thermo-cross-linking when heated to 150° C.

We claim:

1. Glycerol derivatives of general formula (I):

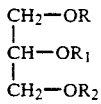

in which R represents an allyl, methylallyl, acryloyl or methacryloyl group, and $R_1$ and $R_2$ are either identical, representing a glyoxyloyl group, or different, representing a hydrogen atom or a glyoxyloyl group.

2. Glycerol derivatives according to claim 1, characterised in that in formula (I), R represents an allyl, acryloyl or methacryloyl group.
3. 3-acryloyloxy-2-glyoxyloyloxy-1-propanol.
4. 1-acryloyloxy-3-glyoxyloyloxy-2-propanol.
5. 3-methacryloyloxy-2-glyoxyloyloxy-1-propanol.
6. 1-methacryloyloxy-3-glyoxyloyloxy-2propanol.
7. 3-allyloxy-2-glyoxyloyloxy-1-propanol.
8. 1-allyloxy-3-glyoxyloyloxy-2-propanol.

* * * * *

UNITED STATES PATENT AND TRADEMARK OFFICE
CERTIFICATE OF CORRECTION

PATENT NO. : 5,093,518
DATED : March 3, 1992
INVENTOR(S) : WILHELM et al.

It is certified that error appears in the above-identified patent and that said Letters Patent is hereby corrected as shown below:

On the title page:

Delete "United States Patent [19]
                Wilheim et al.", insert therefor -- United States Patent [19]
                   Wilhelm et al. --

[75] Inventor:         Delete "Didier Wilheim", insert therefor -- Didier Wilhelm --

Signed and Sealed this

Seventh Day of September, 1993

Attest:

BRUCE LEHMAN

Attesting Officer    Commissioner of Patents and Trademarks